US00PP32410P2

(12) United States Plant Patent
Danziger

(10) Patent No.: US PP32,410 P2
(45) Date of Patent: Oct. 27, 2020

(54) ***OSTEOSPERMUM* PLANT NAMED 'DOSTLEMN'**

(50) Latin Name: *Osteospermum ecklonis*
Varietal Denomination: DOSTLEMN

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,189

(22) Filed: Aug. 22, 2019

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Osteospermum* plant named 'DOSTLEMN' is disclosed, characterized by a trailing growth habit, light yellow flowers, good garden performance during summer and heat tolerance. The new variety is an *Osteospermum*, normally produced as an outdoor garden or container plant.

2 Drawing Sheets

Figure 1:
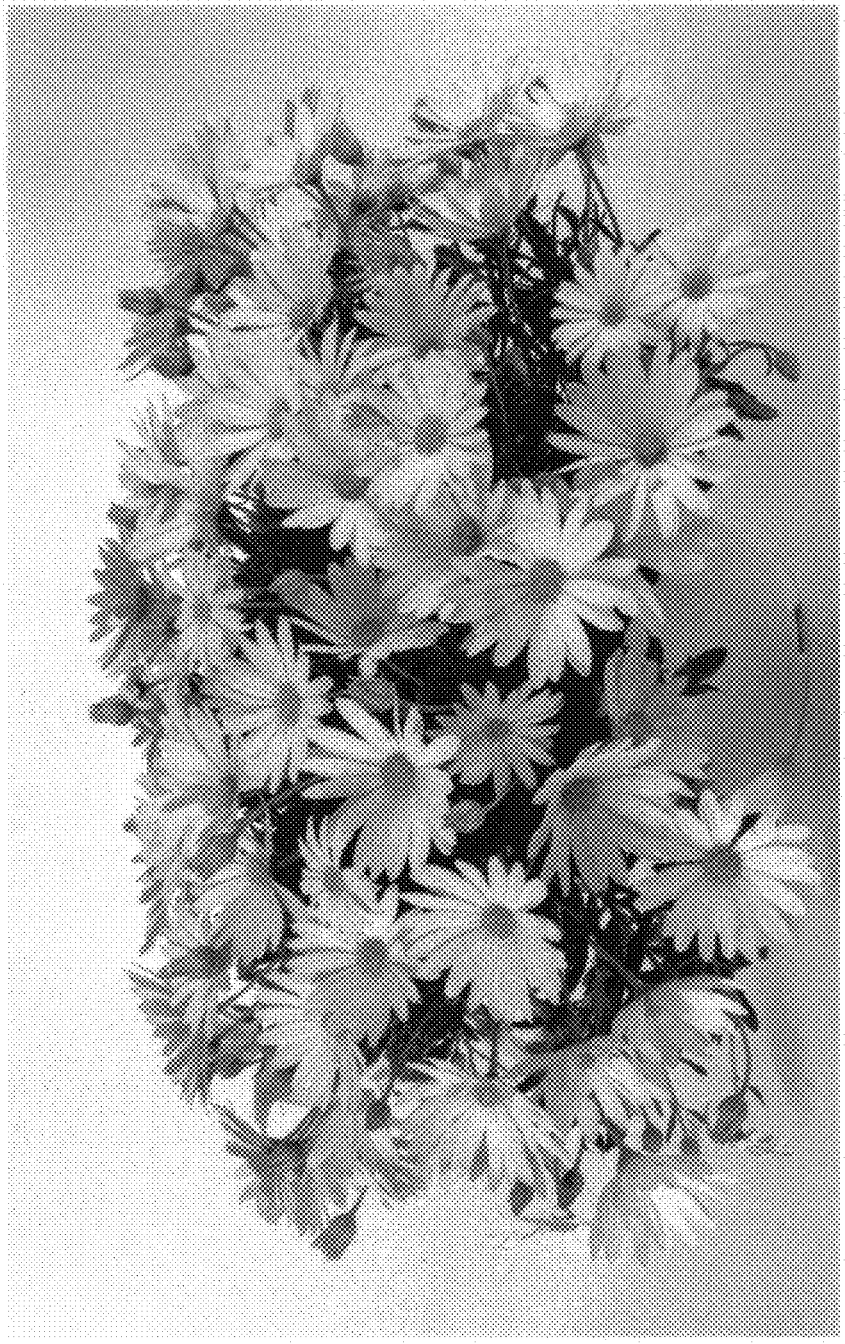

Latin name of the genus and species: *Osteospermum ecklonis.*

Variety denomination: 'DOSTLEMN'.

BACKGROUND OF THE INVENTION

The new *Osteospermum* cultivar is a product of a planned breeding program conducted by the inventor, Gavriel Danziger, in Moshav Mishmar Hashiva, Israel. The objective of the breeding program was to produce new *Osteospermum* varieties for ornamental commercial applications. The open pollination resulting in this new variety was made during February of 2013.

The seed parent is the unpatented, proprietary variety referred to as *Osteospermum* 'OS-Z-172'. The pollen parent is unknown as it was an open pollination breeding program. The new variety was discovered in March of 2014 by the inventor in a group of seedlings resulting from the 2013 crossing, in a research greenhouse in Moshav Mishmar Hashiva, Israel.

Asexual reproduction of the new cultivar was first performed by vegetative tip cuttings. This occurred at a research greenhouse in Moshav Mishmar Hashiva, Israel in April of 2014 and has shown that the unique features of this cultivar are stable and reproduced true to type in more than 10 successive generations. Date of first sale was Sep. 23, 2018, occurring in the United States. This sale was made directly by the inventor or one who obtained the claimed invention directly or indirectly from the inventor. This sale and all public disclosures made between Sep. 23, 2018, and the filing of this application fall within the exception allowed under 102(b)(1).

SUMMARY OF THE INVENTION

The cultivar 'DOSTLEMN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DOSTLEMN'. These characteristics in combination distinguish 'DOSTLEMN' as a new and distinct *Osteospermum* cultivar:

1. Good branching.
2. Light yellow flower.
3. Good garden performance during the summer.

Plants of the new cultivar 'DOSTLEMN' are similar to plants of the seed parent, in most horticultural characteristics, however, plants of the new cultivar 'DOSTLEMN' differ in the following;

1. Plants of the new variety are more trailing than plants of the seed parent.
2. Plants of the new variety have light yellow flowers, while the seed parent has white flowers.
3. Plants of the new variety are more vigorous than plants of the seed parent.

COMMERCIAL COMPARISON

Plants of the new cultivar 'DOSTLEMN' are comparable to the commercial variety *Osteospermum* 'DOSTICPNPL', unpatented. The two *Osteospermum* varieties are similar in most horticultural characteristics; however, the new variety 'DOSTLEMN' differs in the following:

1. Plants of the new variety have a more trailing plant habit than this comparator.
2. Plants of the new variety flower earlier than this comparator.
3. Plants of the new variety have larger flowers than this comparator.
4. Plants of the new variety have a longer flowering time than this comparator.

Plants of the new cultivar 'DOSTLEMN' are comparable to the commercial variety *Osteospermum* 'DOSTIC- MAGM', unpatented. The two *Osteospermum* varieties are similar in most horticultural characteristics; however, the new variety 'DOSTLEMN' differs in the following:

1. Plants of the new variety are more trailing than this comparator.
2. Plants of the new variety flower earlier than this comparator.
3. Plants of the new variety has larger flowers than this comparator.
4. Plants of the new variety have light yellow flowers, while this comparator has red flowers.

BRIEF DESCRIPTION OF THE PHOTOGRAPHS

The accompanying photograph in FIG. 1 illustrates in full color a typical plant of 'DOSTLEMN' grown outdoors, in a 16 cm pot. Age of the plant photographed is approximately 14 weeks from a rooted cutting.

Figure 2:
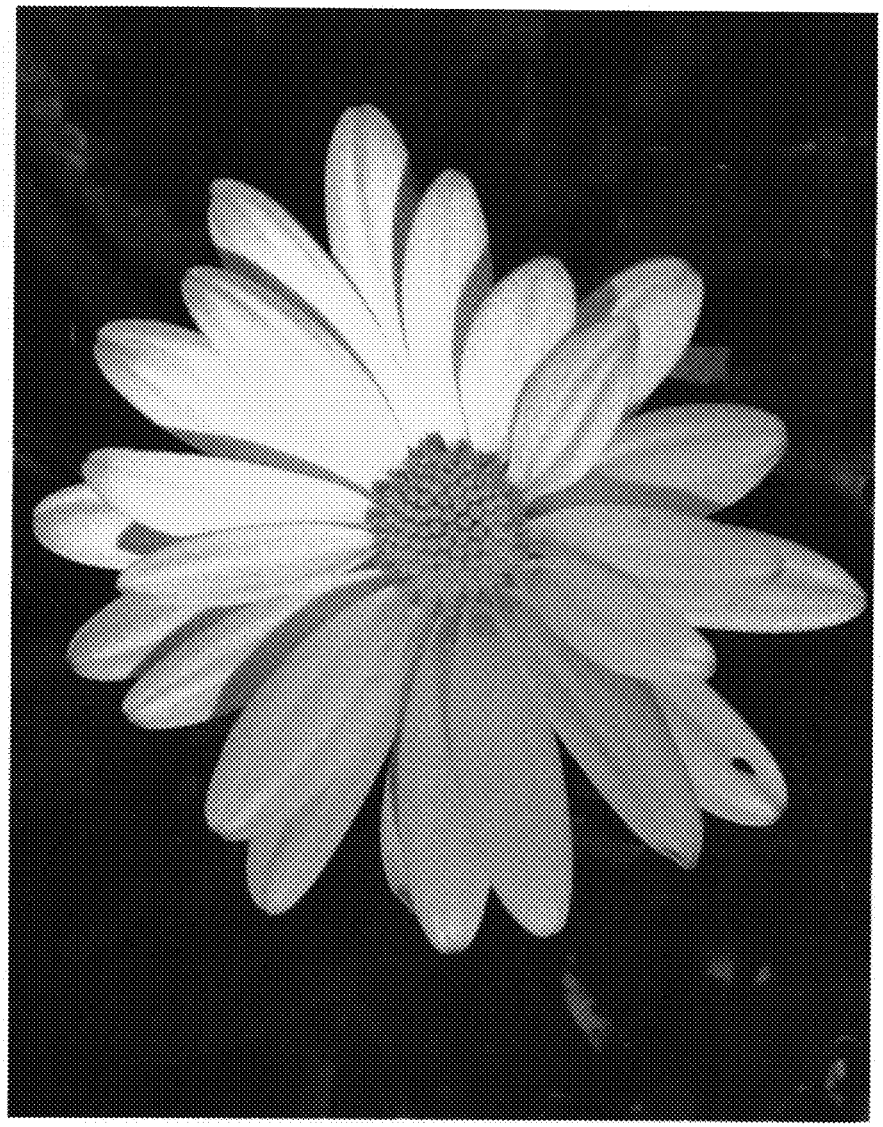

FIG. 2 illustrates a close up of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DOSTLEMN' plants grown outdoors during the Summer in Moshav Mishmar Hashiva, Israel. The growing temperature ranged from 27° C. to 34° C. during the day and from 20° C. to 25° C. during the night. General light conditions are bright, normal sunlight. Measurements and numerical values represent averages of typical plant types.

Botanical classification: *Osteospermum ecklonis* 'DOSTLEMN'.

PROPAGATION

Typical method: Vegetative terminal cuttings.
Time to rooting: 14 days at approximately 18-22° C.

PLANT

Age of plant described: Approximately 100 days from a rooted cutting.
Growth habit: Spreading.
Height: Approximately 14 cm.
Plant spread: Approximately 35 cm.
Growth rate: Moderate growth rate.
Branching characteristics: Freely branching.
Length of lateral branches: Approximately 15 cm.
Diameter of lateral branches: Approximately 0.5 cm.
Texture of lateral branches: Glabrous.
Internode length: Approximately 0.8 cm.
Strength of lateral branches: Flexible.
Color of lateral branches: Near RHS Yellow-Green 145C.
Aspect/angle of branches: 30°.
Number of leaves per lateral branch: Approximately 70.
Root description: Fibrous.

FOLIAGE

Leaf:
- *Arrangement*.—Opposite.
- *Average length*.—Approximately 8 cm.
- *Average width*.—Approximately 2.4 cm.
- *Shape of blade*.—Spatulate.
- *Apex*.—Acute.
- *Base*.—Cuneate.
- *Attachment*.—Absent.
- *Margin*.—Serrate.
- *Texture of top surface*.—Glabrous, leathery.
- *Texture of bottom surface*.—Glabrous.
- *Appearance top surface*.—Shiny.
- *Appearance bottom surface*.—Matte.
- *Leaf internode length*.—Approximately 0.3 cm.
- *Variegation*.—None.
- *Color*.—Young foliage upper side: Near RHS Green 137A. Young foliage under side: Near RHS Green 137D. Mature foliage upper side: Near RHS Green 137A. Mature foliage under side: Near RHS Green 137A.
- *Venation*.—Type: Parallel, only the main vein is visible. Venation color upper side: Near RHS Yellow-Green 144B. Venation color under side: Near RHS Yellow-Green 144C.

Petiole: Absent.

FLOWER

Bud:
- *Bud shape*.—Oblate
- *Bud length*.—Approximately 1 cm.
- *Bud diameter*.—Approximately 1 cm.
- *Bud color*.—Near RHS Yellow-Green 146B.

Inflorescence:
- *Form*.—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward.
- *Paracorolla*.—Absent.

Flower:
- *Diameter of entire flower*.—Approximately 7 cm.
- *Depth of flower*.—Approximately 0.2 cm.
- *Width of disc*.—Approximately 1.1 cm.
- *Depth of disc*.—Approximately 0.5 cm.
- *Receptacle diameter*.—1.2 cm.
- *Receptacle height*.—1 cm.

Ray florets:
- *Number of ray florets*.—Average 26.
- *Length*.—Approximately 3.6 cm.
- *Width*.—Approximately 1 cm.
- *Apex shape*.—Emarginate.
- *Margin*.—Entire.
- *Inward rolling of longitudinal margins*.—Absent all flower heads.

Color:
- *Ray florets*.—Upper surface at first opening: Near RHS Yellow 8C. Upper surface at maturity: Near RHS Yellow 8D. Under surface at fading: Near RHS Yellow 11A. Under surface at first opening: Near RHS Yellow 7C. Under surface at maturity: Near RHS Yellow 10B. Under surface at fading: Near RHS Yellow 10C.

*Disc florets*.—Number of Disc Florets: 125. Length: Approximately 0.7 cm. Width: Approximately 0.1 cm. Shape: Bell-shaped campanulate. Margin: Entire. At first opening: Near RHS Yellow 7A. At maturity: Near RHS Yellow 12A.

Fragrance: None.

Phyllaries:

*Number*.—Approximately 20.
*Length*.—Approximately 1 cm.
*Width*.—Approximately 0.2 cm.
*Shape*.—Ligulate.
*Texture*.—Leathery.
*Apex shape*.—Acute.
*Margin*.—Entire.
*Color*.—Near RHS Green 137C.

Peduncle:

*Peduncle length*.—Approximately 3 cm.
*Peduncle diameter*.—Approximately 0.2 cm.
*Angle*.—Approximately 0° from center of whorl.
*Color*.—Near RHS Yellow-Green 146C.
*Peduncle texture*.—Pubescent.

REPRODUCTIVE ORGANS

Disc florets:

Androecium:

*Stamens*.—90 to 100.
*Anther shape*.—Elliptical.
*Anther length*.—Approximately 1 cm.
*Anther color*.—Near RHS Violet-Blue 92A.
*Pollen quantity*.—Abundant.
*Pollen color*.—Near RHS Yellow-Orange 15B.

Gynoecium: Pistils in disc flowers are degenerated and non-functional.

Ray florets:

*Androecium*.—
*Stamens*.—Stamens in ray florets are degenerated and non-functional.

Gynoecium:

*Pistil number*.—26.
*Pistil shape*.—Needle shape.
*Pistil length*.—Approx. 0.2 cm.
*Style length*.—Approx. 0.1 cm.
*Style color*.—Near RHS Purple 79A.
*Stigma shape*.—Bipartite.
*Stigma color*.—Near RHS Greyed-Orange 177A.
*Ovary diameter*.—0.1 cm.
*Ovary color*.—Near RHS Yellow-Green 150B.

OTHER CHARACTERISTICS

Disease resistance: Neither resistance nor susceptibility to normal diseases and pests of *Osteospermum* have been observed. Typical diseases of *Osteospermum* include: *Botrytis, Pythium, Phytopthera, Rhizoctonia*. Typical pests found in *Osteospermum* include various species of Aphid, Fungus Gnats and Thrips.

Drought tolerance: No drought tolerance.

Temperature tolerance: Good tolerance for heat, to at least 40° C. Frost sensitive.

Fruit/seed production: Seed set has been observed.

*Shape*.—Elliptic.
*Color*.—Near RHS Brown 200C.
*Size*.—Length: 0.6 cm. Diameter: 0.15 cm.

What is claimed is:

1. A new and distinct cultivar of *Osteospermum* plant named 'DOSTLEMN' as herein illustrated and described.

* * * * *